(12) United States Patent
Mizoguchi

(10) Patent No.: US 12,408,816 B2
(45) Date of Patent: Sep. 9, 2025

(54) IMAGING SYSTEM, ENDOSCOPE SYSTEM, AND CONTROL DEVICE

(71) Applicant: OLYMPUS MEDICAL SYSTEMS CORP., Hachioji (JP)

(72) Inventor: Hideaki Mizoguchi, Hachioji (JP)

(73) Assignee: OLYMPUS MEDICAL SYSTEMS CORP., Hachioji (JP)

( * ) Notice: Subject to any disclaimer, the term of this patent is extended or adjusted under 35 U.S.C. 154(b) by 213 days.

(21) Appl. No.: 18/243,806

(22) Filed: Sep. 8, 2023

(65) Prior Publication Data

US 2024/0081617 A1    Mar. 14, 2024

Related U.S. Application Data

(60) Provisional application No. 63/406,528, filed on Sep. 14, 2022.

(51) Int. Cl.
*A61B 1/00* (2006.01)
*A61B 1/05* (2006.01)
*H04N 23/65* (2023.01)

(52) U.S. Cl.
CPC ...... *A61B 1/00029* (2013.01); *A61B 1/00006* (2013.01); *A61B 1/00018* (2013.01); *A61B 1/05* (2013.01)

(58) Field of Classification Search
CPC .. H04N 23/555; H04N 23/65; A61B 1/00006; A61B 1/00018; A61B 1/00027; A61B 1/00029; A61B 1/045; A61B 1/05
See application file for complete search history.

(56) References Cited

U.S. PATENT DOCUMENTS

| | | | | |
|---|---|---|---|---|
| 10,130,246 B2 * | 11/2018 | Sidar | ..................... | A61B 1/0684 |
| 2021/0177241 A1 * | 6/2021 | Tanaka | ............... | A61B 1/00013 |
| 2023/0156362 A1 | 5/2023 | Mizoguchi | | |
| 2023/0225600 A1 * | 7/2023 | Tani | ..................... | H04N 25/709 |
| | | | | 600/118 |

FOREIGN PATENT DOCUMENTS

WO    2022/013953 A1    1/2022

* cited by examiner

*Primary Examiner* — Jessica M Prince
(74) *Attorney, Agent, or Firm* — WHDA, LLP

(57) ABSTRACT

An imaging system includes a camera device and a control device connected to each other by a power source line, a video signal line, and a ground line. An image sensor of the camera device receives, as a distal end voltage, a power source voltage output from the control device to the power source line. An output circuit of the camera device outputs a digital signal indicating a value of the distal end voltage to the video signal line. A calculation circuit of the control device calculates a resistance value of the power source line based on a value of the power source voltage, the value of the distal end voltage indicated by the digital signal, a current value of the power source line, a resistance value of the ground line, and a current value of the ground line.

10 Claims, 9 Drawing Sheets

IMAGING SYSTEM, ENDOSCOPE SYSTEM, AND CONTROL DEVICE

Priority is claimed on U.S. Provisional Patent Application No. 63/406,528, filed on Sep. 14, 2022, the content of which is incorporated herein by reference.

BACKGROUND OF THE INVENTION

Field of the Invention

The present invention relates to an imaging system, an endoscope system, and a control device.

Description of Related Art

An endoscope system includes a camera device (scope) and a control device. The camera device and the control device are connected to each other by a power source line. An image sensor is mounted in the distal end of the camera device. The control device outputs a power source voltage used for driving the image sensor to the power source line. The power source voltage is transferred to the camera device by the power source line and is input to the camera device as a distal end voltage. Due to an influence of both a current flowing through the power source line and the resistance value of the power source line, a voltage drop is generated in the power source line. Therefore, the distal end voltage in the image sensor is lower than the power source voltage output from the control device.

The amount of the current flowing through the power source line changes in accordance with the driving state of the image sensor. Therefore, the control device needs to output a power source voltage having a high value to the power source line in light of the voltage drop generated in accordance with a change of the current. However, a power source voltage having a high value causes an increase of power consumption in the image sensor and an increase of the amount of heat generation in the power source line. Therefore, it is required that the value of the distal end voltage in the image sensor be monitored and a power source voltage having an optimal value be output to the power source line.

A method of calculating the resistance value of the power source line and calculating the value of the distal end voltage in accordance with the following Expression (1) has been considered in order to monitor the value of the distal end voltage.

$$Vcis = Vout - Rc*Ic \quad (1)$$

A voltage value Vcis in Expression (1) indicates the value of the distal end voltage, and a voltage value Vout in Expression (1) indicates the value of the power source voltage. A resistance value Rc in Expression (1) indicates the resistance value of the power source line, and a current value Ic in Expression (1) indicates the value of the current flowing through the power source line.

The resistance value of the power source line changes in accordance with an individual difference of the power source line, passage of time, a change of the temperature, and the like. In the above-described method, it is necessary to calculate the resistance value of the power source line in order to properly control the power source voltage.

A technique disclosed in PCT International Publication No. WO2022/013953 provides a method of calculating a resistance value of a power source line. In the technique, a camera device generates a digital value of a distal end voltage by performing analog-to-digital (AD) conversion. The camera device transmits the generated digital value to a control device. The control device receives the digital value and calculates a resistance value of a power source line in accordance with the following Expression (2).

$$Rc = (Vout - Vcis)/Ic \quad (2)$$

A resistance value Rc in Expression (2) indicates the resistance value of the power source line, and a current value Ic in Expression (2) indicates the value of the current flowing through the power source line. A voltage value Vout in Expression (2) indicates the value of the power source voltage, and a voltage value Vcis in Expression (2) indicates the value of the distal end voltage.

SUMMARY OF THE INVENTION

According to a first aspect of the present invention, an imaging system includes a camera device and a control device connected to each other by a power source line, a video signal line, and a ground line. The camera device includes an image sensor, a voltage measurement circuit, and an output circuit. The image sensor receives, as a distal end voltage, a power source voltage output from the control device to the power source line and generates a video signal by using the distal end voltage. The voltage measurement circuit measures a value of the distal end voltage. The output circuit outputs the video signal to the video signal line and outputs a digital signal indicating the value of the distal end voltage to the video signal line. The control device includes a voltage generation circuit, a current measurement unit circuit, a reception circuit, a calculation circuit, and a voltage adjustment circuit. The voltage generation circuit generates the power source voltage and outputs the generated power source voltage to the power source line. The current measurement circuit measures a current value of the power source line. The reception circuit receives the video signal and the digital signal output from the camera device to the video signal line. The calculation circuit calculates a resistance value of the power source line based on a value of the power source voltage, the value of the distal end voltage indicated by the digital signal, the current value of the power source line, a resistance value of the ground line, and a current value of the ground line. The voltage adjustment circuit adjusts a value of the power source voltage based on the resistance value of the power source line, the current value of the power source line, the resistance value of the ground line, and the current value of the ground line such that the value of the distal end voltage nears a target value.

According to a second aspect of the present invention, in the first aspect, the power source line may include a first power source line and a second power source line. The image sensor may receive, as a first distal end voltage, a first power source voltage output from the control device to the first power source line and may receive, as a second distal end voltage, a second power source voltage output from the control device to the second power source line. A value of the second power source voltage may be different from a value of the first power source voltage. The voltage measurement circuit may measure a value of the first distal end voltage and a value of the second distal end voltage. The output circuit may output a first digital signal indicating the value of the first distal end voltage and a second digital signal indicating the value of the second distal end voltage to the video signal line. The voltage generation circuit may generate the first power source voltage and the second power source voltage. The voltage generation circuit may output the generated first power source voltage to the first power source line and may output the generated second power source voltage to the second power source line. The current measurement circuit may measure a current value of the first power source line and a current value of the second power source line. The reception circuit may receive the first digital signal and the second digital signal. The calculation circuit may calculate a resistance value of the first power source line based on the value of the first power source voltage, the value of the first distal end voltage indicated by the first digital signal, the current value of the first power source line, the resistance value of the ground line, and the current value of the ground line. The calculation circuit may calculate a resistance value of the second power source line based on the value of the second power source voltage, the value of the second distal end voltage indicated by the second digital signal, the current value of the second power source line, the resistance value of the ground line, and the current value of the ground line. The voltage adjustment circuit may adjust the value of the first power source voltage based on the resistance value of the first power source line, the current value of the first power source line, the resistance value of the ground line, and the current value of the ground line such that the value of the first distal end voltage nears a first target value. The voltage adjustment circuit may adjust the value of the second power source voltage based on the resistance value of the second power source line, the current value of the second power source line, the resistance value of the ground line, and the current value of the ground line such that the value of the second distal end voltage nears a second target value.

According to a third aspect of the present invention, in the second aspect, the calculation circuit may calculate the resistance value of the ground line based on the value of the first power source voltage, the value of the first distal end voltage indicated by the first digital signal, and the current value of the ground line.

According to a fourth aspect of the present invention, in the second aspect, the voltage generation circuit may output the first power source voltage to the first power source line in a first period and a second period and may output the second power source voltage to the second power source line in the first period and the second period. A current value of the first power source line in the second period may be the same as a current value of the first power source line in the first period. A current value of the second power source line in the second period may be different from a current value of the second power source line in the first period. The calculation circuit may calculate the resistance value of the ground line based on the value of the first power source voltage in each of the first period and the second period, the value of the first distal end voltage indicated by the first digital signal in each of the first period and the second period, and the current value of the ground line in each of the first period and the second period.

According to a fifth aspect of the present invention, in the fourth aspect, the first period and the second may be included in a blanking period of the image sensor.

According to a sixth aspect of the present invention, in the second aspect, the calculation circuit may calculate the current value of the ground line based on the current value of the first power source line and the current value of the second power source line.

According to a seventh aspect of the present invention, in the second aspect, one of the first distal end voltage and the second distal end voltage is provided to a digital circuit included in the image sensor. The other of the first distal end voltage and the second distal end voltage may be provided to an analog circuit included in the image sensor.

According to an eighth aspect of the present invention, in the first aspect, the resistance value of the ground line may be the same as the resistance value of the power source line.

According to a ninth aspect of the present invention, an endoscope system includes a scope to be inserted into a living body and includes the imaging device. The camera device is disposed in a distal end of the scope.

According to a tenth aspect of the present invention, a control device is used in an imaging system including a camera device and the control device connected to each other by a power source line, a video signal line, and a ground line. The control device includes a voltage generation circuit, a current measurement circuit, a reception circuit, a calculation circuit, and a voltage adjustment circuit. The voltage generation circuit generates a power source voltage and outputs the generated power source voltage to the power source line. The current measurement circuit measures a current value of the power source line. The reception circuit receives a video signal and a digital signal output from the camera device to the video signal line. The video signal is generated by an image sensor of the camera device. The image sensor receives, as a distal end voltage, the power source voltage output from the control device to the power source line and generates the video signal by using the distal end voltage. The digital signal indicates a value of the distal end voltage. The calculation circuit calculates a resistance value of the power source line based on a value of the power source voltage, the value of the distal end voltage indicated by the digital signal, the current value of the power source line, a resistance value of the ground line, and a current value of the ground line. The voltage adjustment circuit adjusts a value of the power source voltage based on the resistance value of the power source line, the current value of the power source line, the resistance value of the ground line, and the current value of the ground line such that the value of the distal end voltage nears a target value.

DETAILED DESCRIPTION OF THE INVENTION

Hereinafter, embodiments of the present invention will be described with reference to the drawings. Each of the embodiments will be described in detail by using an endoscope system as an example of an imaging system.

First Embodiment

Figure 1:
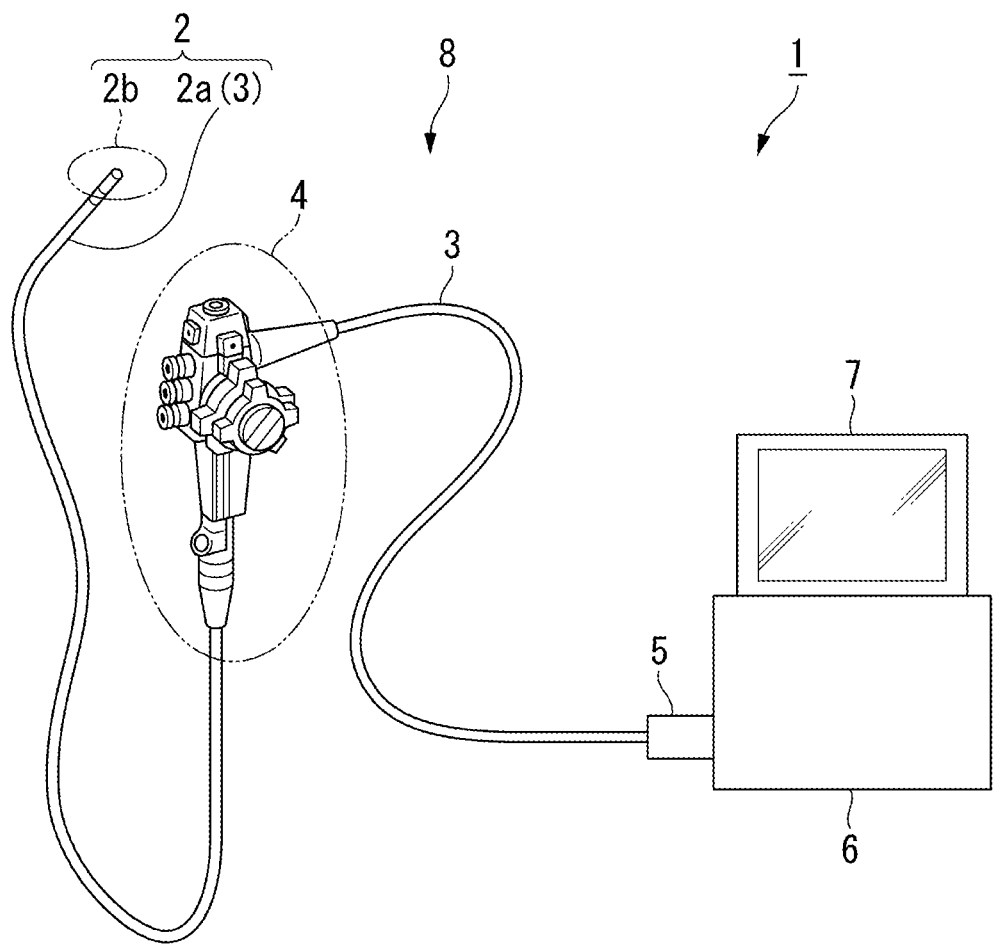
FIG. 1 is a schematic diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 2, a transmission cable 3, an operation unit 4, a connector unit 5, a control unit 6, and a display device 7. The endoscope insertion unit 2, the transmission cable 3, the operation unit 4, and the connector unit 5 constitute a scope 8.

Figure 2:
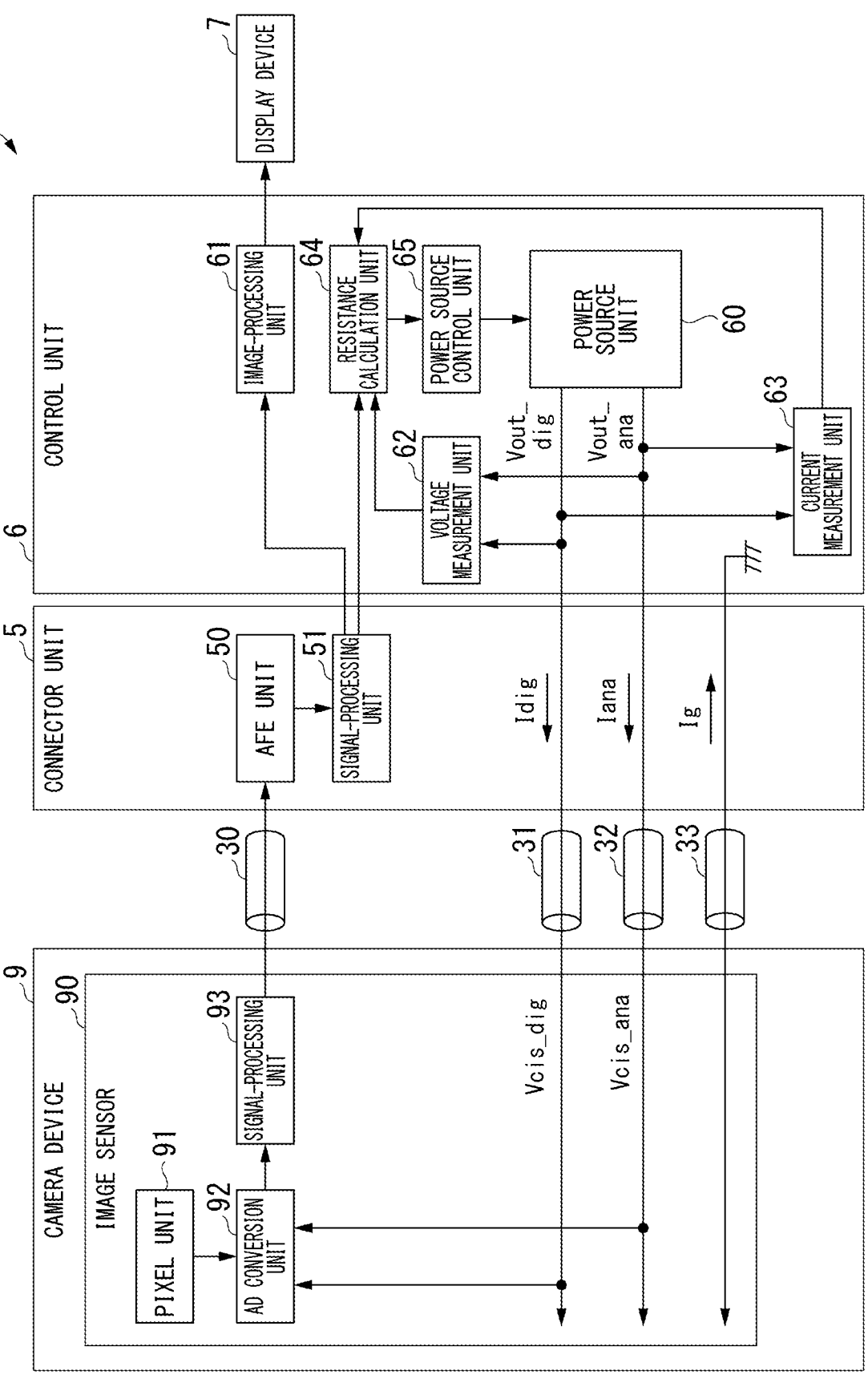
FIG. 2 is a block diagram showing a configuration of the endoscope system according to the first embodiment of the present invention.

The endoscope insertion unit 2 includes an insertion unit 2a. The insertion unit 2a is part of the transmission cable 3. The insertion unit 2a is to be inserted inside a living body, which is a subject. The endoscope insertion unit 2 generates a video signal by imaging the inside of the subject. The endoscope insertion unit 2 outputs the generated video signal to the control unit 6. A camera device 9 shown in FIG. 2 is disposed in a distal end 2b of the insertion unit 2a. In the insertion unit 2a, the operation unit 4 is connected to the end part opposite the distal end 2b. The operation unit 4 receives various operations for the endoscope insertion unit 2 from a user.

The transmission cable 3 connects the camera device 9 and the connector unit 5. The video signal generated by the camera device 9 is output to the connector unit 5 via the transmission cable 3.

The connector unit 5 is connected to the endoscope insertion unit 2 and the control unit 6. The connector unit 5 performs predetermined processing on the video signal output from the endoscope insertion unit 2. The connector unit 5 outputs the video signal to the control unit 6.

The control unit 6 performs image processing on the video signal output from the connector unit 5. Furthermore, the control unit 6 centrally controls the entire endoscope system 1.

The display device 7 displays a video based on the video signal processed by the control unit 6. In addition, the display device 7 displays various kinds of information related to the endoscope system 1.

FIG. 2 shows an internal configuration of the endoscope system 1. The endoscope system 1 shown in FIG. 2 includes the camera device 9, the connector unit 5, and the control unit 6. The camera device 9 is disposed in the distal end 2b of the scope 8. The connector unit 5 and the control unit 6 constitute a control device 10. The operation unit 4 is not shown in FIG. 2. The transmission cable 3 shown in FIG. 1 includes a video signal line 30, a power source line 31, a power source line 32, and a ground line 33 shown in FIG. 2.

The endoscope system 1 includes a light source device that generates illumination light emitted to the subject. The light source device is omitted in FIG. 2. The camera device 9 includes an image sensor 90. The image sensor 90 includes a pixel unit 91, an AD conversion unit 92, and a signal-processing unit 93 (output circuit).

The connector unit 5 includes an analog front end (AFE) unit 50 (reception circuit) and a signal-processing unit 51. All or part of the configuration of the connector unit 5 shown in FIG. 2 may be disposed in the operation unit 4 or the control unit 6.

The control unit 6 includes a power source unit 60 (voltage generation circuit), an image-processing unit 61, a voltage measurement unit 62 (voltage measurement circuit), a current measurement unit 63 (current measurement circuit), a resistance calculation unit 64 (calculation circuit), and a power source control unit 65 (power source adjustment circuit). All or part of the configuration of the control unit 6 shown in FIG. 2 may be disposed in the operation unit 4 or the connector unit 5.

A schematic configuration of the endoscope system 1 will be described. The camera device 9 and the control unit 6 are connected to each other by the power source line 31, the power source line 32, the video signal line 30, and the ground line 33. The image sensor 90 receives, as a distal end voltage Vcis_dig (Vcis_ana), a power source voltage Vout_dig (Vout_ana) output from the control unit 6 to the power source line 31 (power source line 32) and generates a video signal by using the distal end voltage Vcis_dig (Vcis_ana). The AD conversion unit 92 measures a value of the distal end voltage Vcis_dig (Vcis_ana). The signal-processing unit 93 outputs the video signal to the video signal line 30 and outputs a digital signal indicating the value of the distal end voltage Vcis_dig (Vcis_ana) to the video signal line 30 (power source line 32). The power source unit 60 generates the power source voltage Vout_dig (Vout_ana) and outputs the generated power source voltage Vout_dig (Vout_ana) to the power source line 31. The current measurement unit 63 measures a current value of the power source line 31 (power source line 32). The AFE unit 50 receives the video signal and the digital signal output from the camera device 9 to the video signal line 30. The resistance calculation unit 64 calculates a resistance value of the power source line 31 (power source line 32) based on the value of the power source voltage Vout_dig (Vout_ana), the value of the distal end voltage Vcis_dig (Vcis_ana) indicated by the digital signal, the current value of the power source line 31 (power source line 32), a resistance value of the ground line 33, and a current value of the ground line 33. The power source control unit 65 adjusts the value of the power source voltage Vout_dig (Vout_ana) based on the resistance value of the power source line 31 (power source line 32), the current value of the power source line 31 (power source line 32), the resistance value of the ground line 33, and the current value of the ground line 33 such that the value of the distal end voltage Vcis_dig (Vcis_ana) nears a target value.

A detailed configuration of the endoscope system 1 will be described. For example, the power source unit 60 includes a voltage regulator. The power source unit 60 generates the power source voltage Vout_dig and the power source voltage Vout_ana. The power source voltage Vout_dig is a direct-current (DC) voltage to be provided to a digital circuit included in the image sensor 90. The power source voltage Vout_ana is a DC voltage to be provided to an analog circuit included in the image sensor 90. In general, the value of the power source voltage Vout_dig is greater than that of the power source voltage Vout_ana. The value of the power source voltage Vout_ana is greater than that (0 V) of a ground voltage (reference voltage). For example, the value of the power source voltage Vout_dig is 1 V or the like, and the value of the power source voltage Vout_ana is 2.7 V or the like.

The power source unit 60 is connected to the power source line 31 and the power source line 32. The power source unit 60 outputs the power source voltage Vout_dig to the power source line 31 and outputs the power source voltage Vout_ana to the power source line 32. The power source line 31 and the power source line 32 are signal lines disposed in the transmission cable 3. The power source line 31 transfers the power source voltage Vout_dig to the camera device 9. The power source line 32 transfers the power source voltage Vout_ana to the camera device 9.

The power source voltage Vout_dig transferred by the power source line 31 and the power source voltage Vout_ana transferred by the power source line 32 are input to the camera device 9. The image sensor 90 is connected to the power source line 31 and the power source line 32. The power source voltage Vout_dig is provided as the distal end voltage Vcis_dig to each circuit in the image sensor 90. For example, the distal end voltage Vcis_dig is output to the signal-processing unit 93. In addition, the distal end voltage Vcis_dig is output to a register that stores a value used for controlling the image sensor 90. The power source voltage Vout_ana is provided as the distal end voltage Vcis_ana to each circuit in the image sensor 90. For example, the distal end voltage Vcis_ana is output to the pixel unit 91 and the AD conversion unit 92.

A current Idig flows through the power source line 31, and a current Iana flows through the power source line 32. A voltage drop is generated due to the DC resistance of the power source line 31, and the distal end voltage Vcis_dig is attenuated. Therefore, the value of the distal end voltage Vcis_dig is less than that of the power source voltage Vout_dig in the control unit 6. Similarly, a voltage drop is generated due to the DC resistance of the power source line 32, and the distal end voltage Vcis_ana is attenuated. Therefore, the value of the distal end voltage Vcis_ana is less than that of the power source voltage Vout_ana in the control unit 6.

The ground line 33 is a signal line disposed in the transmission cable 3. The ground line 33 transfers the ground voltage from the control unit 6 to the camera device 9. The image sensor 90 is connected to the ground line 33. The ground voltage transferred by the ground line 33 is input to the camera device 9 and is provided to each circuit in the image sensor 90. A current Ig flows through the ground line 33. A voltage drop is generated due to the DC resistance of the ground line 33. Therefore, the value of the ground voltage in the camera device 9 is different from that in the control unit 6.

The image sensor 90 is a complementary metal-oxide semiconductor (CMOS) sensor or the like. The pixel unit 91 includes two or more pixels and is driven based on the distal end voltage Vcis_ana. The pixel unit 91 generates a pixel signal having a voltage generated based on the distal end voltage Vcis_ana and the ground voltage. The pixel unit 91 outputs the pixel signal in a video output period and stops the output of the pixel signal in a blanking period.

The AD conversion unit 92 performs AD conversion on the pixel signal output from the pixel unit 91 and generates a digital pixel signal. The AD conversion unit 92 performs the AD conversion on the distal end voltage Vcis_dig and generates a digital signal indicating a value of the distal end voltage Vcis_dig. The AD conversion unit 92 performs the AD conversion on the distal end voltage Vcis_ana and generates a digital signal indicating a value of the distal end voltage Vcis_ana.

After the power source of the endoscope system 1 is turned on and the power source unit 60 starts generation of the power source voltage Vout_dig and the power source voltage Vout_ana, a resistance calculation period for calculating the resistance value (ground resistance value) of the ground line 33 is set. For example, the AD conversion unit 92 generates the digital signal in the resistance calculation period before the pixel unit 91 generates the pixel signal. The AD conversion unit 92 may generate the digital signal in the blanking period.

The signal-processing unit 93 processes the digital pixel signal output from the AD conversion unit 92 and generates a video signal. For example, the signal-processing unit 93 performs noise reduction, amplification processing, and the like on the digital pixel signal. The signal-processing unit 93 outputs the video signal to the video signal line 30. In addition, the signal-processing unit 93 outputs a digital signal indicating a value of each of the power source voltage Vout_dig and the power source voltage Vout_ana to the video signal line 30.

At least one of the AD conversion unit 92 and the signal-processing unit 93 may be disposed in a different substrate from that in which the image sensor 90 is disposed. In other words, at least one of the AD conversion unit 92 and the signal-processing unit 93 may be disposed outside the image sensor 90.

The video signal line 30 is a signal line disposed in the transmission cable 3. The video signal line 30 transfers the video signal and the digital signal output from the signal-processing unit 93 to the connector unit 5.

The AFE unit 50 receives the video signal and the digital signal transferred by the video signal line 30. The AFE unit 50 performs processing such as noise elimination on the video signal and the digital signal. The signal-processing unit 51 performs gain-up processing or the like on the video signal and the digital signal output from the AFE unit 50. The signal-processing unit 51 outputs the video signal to the image-processing unit 61 and outputs the digital signal to the resistance calculation unit 64.

The image-processing unit 61 performs demosaicing processing, white balance adjustment processing, γ correction processing, and the like on the video signal. The image-processing unit 61 output the video signal to the display device 7.

The voltage measurement unit 62 measures a value of the power source voltage Vout_dig output from the power source unit 60 to the power source line 31 and measures a value of the power source voltage Vout_ana output from the power source unit 60 to the power source line 32. The voltage measurement unit 62 outputs the value of the power source voltage Vout_dig and the value of the power source voltage Vout_ana to the resistance calculation unit 64.

The current measurement unit 63 measures a value of the current Idig flowing through the power source line 31 and measures a value of the current Iana flowing through the power source line 32. The current measurement unit 63 outputs a current value of the power source line 31 and a current value of the power source line 32 to the resistance calculation unit 64.

The resistance calculation unit 64 calculates the resistance value of the ground line 33 based on the value of the power source voltage Vout_dig, the value of the distal end voltage Vcis_dig indicated by the digital signal, and the current value of the ground line 33. The resistance calculation unit 64 can calculate the current value of the ground line 33 by adding the current value of the power source line 31 and the current value of the power source line 32. In a case in which the ground line 33 is constituted by a single signal line and a current as the ground current flows only through the ground line 33, the camera device 9 may include a current measurement circuit that measures the ground current.

The resistance calculation unit 64 calculates the resistance value of the power source line 31 based on the value of the power source voltage Vout_dig, the value of the distal end voltage Vcis_dig indicated by the digital signal, the current value of the power source line 31, the resistance value of the ground line 33, and the current value of the ground line 33. In addition, the resistance calculation unit 64 calculates the resistance value of the power source line 32 based on the value of the power source voltage Vout_ana, the value of the distal end voltage Vcis_ana indicated by the digital signal, the current value of the power source line 32, the resistance value of the ground line 33, and the current value of the ground line 33. A method of calculating the resistance value of the ground line 33, the resistance value of the power source line 31, and the resistance value of the power source line 32 will be described later. The resistance calculation unit 64 outputs the resistance value of the power source line 31 and the resistance value of the power source line 32 to the power source control unit 65.

The resistance calculation unit 64 is a digital circuit including at least one of a processor and a logic circuit. For example, the processor is a central processing unit (CPU). For example, the logic circuit is at least one of an application-specific integrated circuit (ASIC) or a field-programmable gate array (FPGA). The resistance calculation unit 64 may include one or a plurality of processors. The resistance calculation unit 64 may include one or a plurality of logic circuits.

The resistance calculation unit 64 may read a program and execute the read program. The program includes commands defining the operations of the resistance calculation unit 64. In other words, the functions of the resistance calculation unit 64 may be realized by software. The program may be transmitted from a computer storing the program to the endoscope system 1 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. The program described above may realize some of the functions described above. In addition, the program described above may be a differential file (differential program). The functions described above may be realized by a combination of a program that has already been recorded in a computer and a differential program.

The power source control unit 65 controls the power source unit 60 based on the resistance value of the power source line 31, the current value of the power source line 31, the resistance value of the ground line 33, and the current value of the ground line 33. By doing this, the power source control unit 65 adjusts the value of the power source voltage Vout_dig to be generated by the power source unit 60. In addition, the power source control unit 65 controls the power source unit 60 based on the resistance value of the power source line 32, the current value of the power source line 32, the resistance value of the ground line 33, and the current value of the ground line 33. By doing this, the power source control unit 65 adjusts the value of the power source voltage Vout_ana to be generated by the power source unit 60.

The transmission cable 3 may include three or more power source lines. Two of the three or more power source lines correspond to the power source line 31 and the power source line 32.

Figure 3:
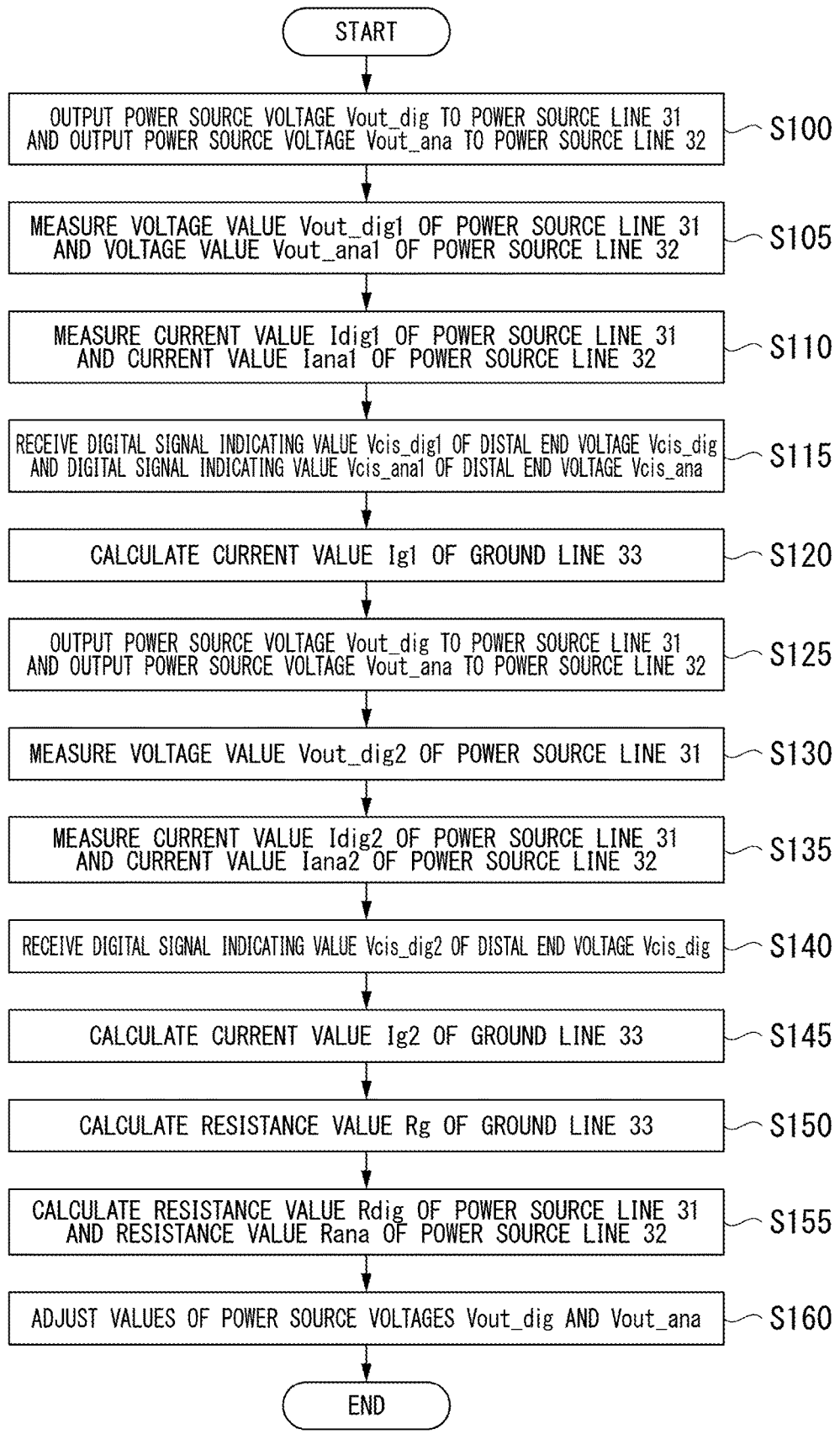
FIG. 3 is a flow chart showing a procedure of an operation of a control unit included in the endoscope system according to the first embodiment of the present invention.

FIG. 3 shows a procedure of an operation of the control unit 6 related to adjustment of the power source voltage Vout_dig and the power source voltage Vout_ana. The operation of the control unit 6 will be described by using FIG. 3.

The resistance calculation period includes a first period and a second period. The power source unit 60 generates the power source voltage Vout_dig and the power source voltage Vout_ana in the first period. The power source unit 60 outputs the power source voltage Vout_dig to the power source line 31 and outputs the power source voltage Vout_ana to the power source line 32 (Step S100).

After Step S100, the voltage measurement unit 62 measures a value Vout_dig1 of the power source voltage Vout_dig in the power source line 31 and measures a value Vout_ana1 of the power source voltage Vout_ana in the power source line 32. The voltage measurement unit 62 outputs the value Vout_dig1 and the value Vout_ana1 to the resistance calculation unit 64 (Step S105).

After Step S105, the current measurement unit 63 measures a current value Idig1 of the power source line 31 and a current value Iana1 of the power source line 32 and outputs the current value Idig1 and the current value Iana1 to the resistance calculation unit 64 (Step S110).

After Step S110, the AFE unit 50 receives a digital signal indicating a value Vcis_dig1 of the distal end voltage Vcis_dig in the first period and processes the digital signal. In addition, the AFE unit 50 receives a digital signal indicating a value Vcis_ana1 of the distal end voltage Vcis_ana in the first period and processes the digital signal. Each digital signal processed by the AFE unit 50 is output to the signal-processing unit 51. The signal-processing unit 51 processes each digital signal and outputs each digital signal to the resistance calculation unit 64 (Step S115).

After Step S115, the resistance calculation unit 64 calculates a current value Ig1 of the ground line 33 by adding the current value Idig1 of the power source line 31 and the current value Iana1 of the power source line 32 (Step S120).

The first period is completed, and the second period is started. The power source unit 60 generates the power source voltage Vout_dig and the power source voltage Vout_ana in the second period. The power source unit 60 outputs the power source voltage Vout_dig to the power source line 31 and outputs the power source voltage Vout_ana to the power source line 32 (Step S125).

After Step S125, the voltage measurement unit 62 measures a value Vout_dig2 of the power source voltage Vout_dig in the power source line 31 and outputs the value Vout_dig2 to the resistance calculation unit 64 (Step S130).

After Step S130, the current measurement unit 63 measures a current value Idig2 of the power source line 31 and a current value Iana2 of the power source line 32 and outputs the current value Idig2 and the current value Iana2 to the resistance calculation unit 64 (Step S135).

After Step S135, the AFE unit 50 receives a digital signal transferred by the video signal line 30 and processes the digital signal. The digital signal indicates a value Vcis_dig2 of the distal end voltage Vcis_dig in the second period. The digital signal is output to the signal-processing unit 51. The signal-processing unit 51 processes the digital signal and outputs the digital signal to the resistance calculation unit 64 (Step S140).

After Step S140, the resistance calculation unit 64 calculates a current value Ig2 of the ground line 33 by adding the current value Idig2 of the power source line 31 and the current value Iana2 of the power source line 32 (Step S145).

Figure 4:
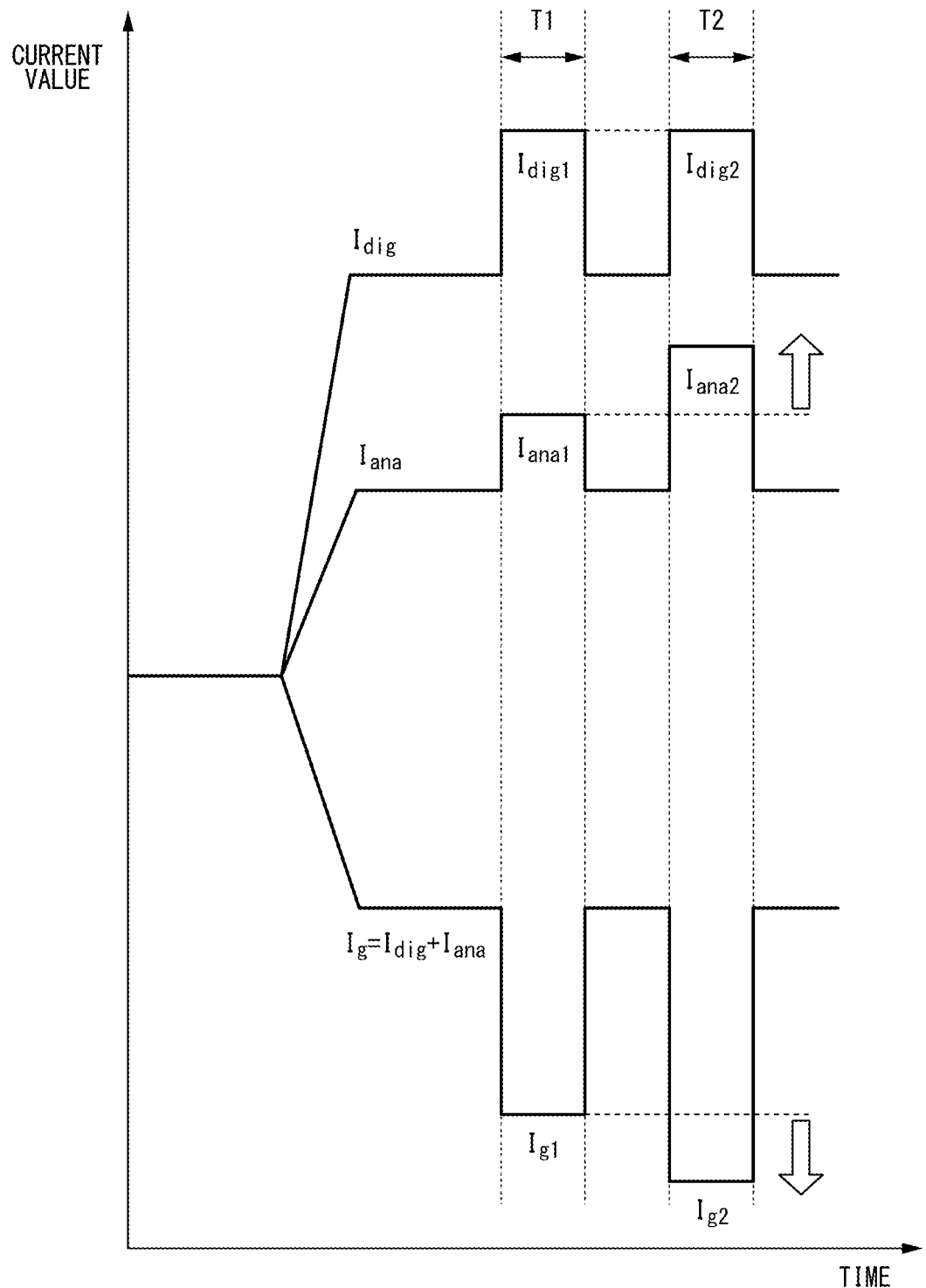
FIG. 4 is a timing chart showing waveforms of currents flowing through a transmission cable included in the endoscope system according to the first embodiment of the present invention.

FIG. 4 shows waveforms of the current Idig, the current Iana, and the current 1g. The horizontal axis in FIG. 4 indicates time, and the vertical axis in FIG. 4 indicates a current value.

The power source unit 60 outputs the power source voltage Vout_dig to the power source line 31 such that a value Idig1 of the current Idig in a first period T1 and a value Idig2 of the current Idig in a second period T2 are the same. For example, a value Vout_dig2 of the power source voltage Vout_dig in the second period T2 is the same as a value Vout_dig1 of the power source voltage Vout_dig in the first period T1.

The power source unit 60 outputs the power source voltage Vout_ana to the power source line 32 such that a value Iana1 of the current Iana in the first period T1 and a value Iana2 of the current Iana in the second period T2 are different. For example, a value Vout_ana2 of the power source voltage Vout_ana in the second period T2 is different from a value Vout_ana1 of the power source voltage Vout_ana in the first period T1.

In the example shown in FIG. 4, the value Iana2 of the current Iana in the second period T2 is greater than the value Iana1 of the current Iana in the first period T1. The value Iana2 of the current Iana in the second period T2 may be less than the value Iana1 of the current Iana in the first period T1.

The current Ig is the sum of the current Idig and the current Iana. The value of the current Ig in the first period T1 is Ig1, and the value of the current Ig in the second period T2 is Ig2.

After Step S145, the resistance calculation unit 64 calculates a resistance value Rg of the ground line 33 based on the values Vout_dig1 and Vout_dig2 of the power source voltage Vout_dig, the values Vcis_dig1 and Vcis_dig2 of the distal end voltage Vcis_dig, and the current values Ig1 and Ig2 of the ground line 33 (Step S150).

The following Expression (4) shows the value Vout_dig1 of the power source voltage Vout_dig in the first period.

$$V_{out\_dig1} = R_{dig}I_{dig1} + V_{cis\_dig1} + R_g I_{g1} \quad (4)$$

A resistance value Rdig in Expression (4) indicates the resistance value of the power source line 31, and a current value Idig1 in Expression (4) indicates the current value of the power source line 31 in the first period. A voltage value Vcis_dig1 in Expression (4) indicates the value of the distal end voltage Vcis_dig in the first period. A resistance value Rg in Expression (4) indicates the resistance value of the ground line 33, and a current value Ig1 in Expression (4) indicates the current value of the ground line 33 in the first period.

The following Expression (5) shows the value Vout_dig2 of the power source voltage Vout_dig in the second period.

$$V_{out\_dig2} = R_{dig}I_{dig2} + V_{cis\_dig2} + R_g I_{g2} \quad (5)$$

A resistance value Rdig in Expression (5) indicates the resistance value of the power source line 31, and a current value Idig2 in Expression (5) indicates the current value of the power source line 31 in the second period. A voltage value Vcis_dig2 in Expression (5) indicates the value of the distal end voltage Vcis_dig in the second period. A resistance value Rg in Expression (5) indicates the resistance value of the ground line 33, and a current value Ig2 in Expression (5) indicates the current value of the ground line 33 in the second period.

The current value Idig2 is the same as the current value Idig1. Accordingly, the following Expression (6) showing a difference between Expression (4) and Expression (5) is obtained.

$$V_{out\_dig1} - V_{out\_dig2} = (V_{cis\_dig1} - V_{cis\_dig2}) + R_g(I_{g1} - I_{g2}) \quad (6)$$

By modifying Expression (6), the following Expression (7) is obtained. The resistance calculation unit 64 calculates the resistance value Rg of the ground line 33 in accordance with Expression (7) in Step S150.

$$R_g = \frac{(V_{out\_dig1} - V_{out\_dig2}) - (V_{cis\_dig1} - V_{cis\_dig2})}{I_{g1} - I_{g2}} \quad (7)$$

After Step S150, the resistance calculation unit 64 calculates the resistance value Rdig of the power source line 31 based on the value of the power source voltage Vout_dig, the value of the distal end voltage Vcis_dig, the current value of the power source line 31, the resistance value Rg of the ground line 33, and the current value Ig of the ground line 33. In addition, the resistance calculation unit 64 calculates the resistance value Rana of the power source line 32 based on the value of the power source voltage Vout_ana, the value of the distal end voltage Vcis_ana, the current value of the power source line 32, the resistance value Rg of the ground line 33, and the current value Ig of the ground line 33. The resistance calculation unit 64 outputs the resistance value Rdig of the power source line 31 and the resistance value Rana of the power source line 32 to the power source control unit 65 (Step S155).

By modifying Expression (4), the following Expression (8) is obtained. The resistance calculation unit 64 calculates the resistance value Rdig of the power source line 31 in accordance with Expression (8) in Step S155.

$$R_{dig} = \frac{V_{out\_dig1} - V_{cis\_dig1} - R_g I_{g1}}{I_{dig1}} \quad (8)$$

Expression (8) uses the value Vout_dig1 of the power source voltage Vout_dig in the first period, the value Vcis_dig1 of the distal end voltage Vcis_dig in the first period, the resistance value Rg of the ground line 33, the current value Ig1 of the ground line 33 in the first period, and the current value Idig1 of the power source line 31 in the first period. The resistance calculation unit 64 may calculate the resistance value Rdig of the power source line 31 by using the value Vout_dig2 of the power source voltage Vout_dig in the second period, the value Vcis_dig2 of the distal end voltage Vcis_dig in the second period, the resistance value Rg of the ground line 33, the current value Ig2 of the ground line 33 in the second period, and the current value Idig2 of the power source line 31 in the second period.

The following Expression (9) is a similar expression to Expression (8). The resistance calculation unit 64 calculates the resistance value Rana of the power source line 32 in accordance with Expression (9) in Step S155.

$$R_{ana} = \frac{V_{out\_ana1} - V_{cis\_ana1} - R_g I_{g1}}{I_{ana1}} \quad (9)$$

Expression (9) uses the value Vout_ana1 of the power source voltage Vout_ana in the first period, the value Vcis_ana1 of the distal end voltage Vcis_ana in the first period, the resistance value Rg of the ground line 33, the current value Ig1 of the ground line 33 in the first period, and the current value Iana1 of the power source line 32 in the first period. The resistance calculation unit 64 may calculate the resistance value Rana of the power source line 32 by using the value Vout_ana2 of the power source voltage Vout_ana in the second period, the value Vcis_ana2 of the distal end voltage Vcis_ana in the second period, the resistance value Rg of the ground line 33, the current value Ig2 of the ground line 33 in the second period, and the current value Iana2 of the power source line 32 in the second period.

After Step S155, the power source control unit 65 controls the power source unit 60 based on the resistance value Rdig of the power source line 31, the current value of the power source line 31, the resistance value Rg of the ground line 33, and the current value of the ground line 33. By doing this, the power source control unit 65 adjusts the value of the power source voltage Vout_dig. In addition, the power source control unit 65 controls the power source unit 60 based on the resistance value Rana of the power source line 32, the current value of the power source line 32, the resistance value Rg of the ground line 33, and the current value of the ground line 33. By doing this, the power source control unit 65 adjusts the value of the power source voltage Vout_ana (Step S160).

The following Expression (10) indicates a value Vout_digc of the power source voltage Vout_dig. The power source control unit 65 adjusts the value Vout_digc of the power source voltage Vout_dig in accordance with Expression (10) in Step S160.

$$V_{out\_digc}=R_{dig}I_{dig}+V_{tar\_dig}+R_{g}I_{g} \quad (1)$$

A resistance value Rdig in Expression (10) is the same as the resistance value Rdig in Expression (8). The current measurement unit 63 measures the current value Idig of the power source line 31 and the current value Iana of the power source line 32 and outputs the current value Idig and the current value Iana to the resistance calculation unit 64. This current value Idig is used in Expression (10). A value Vtar_dig in Expression (10) indicates a target value (for example, 1 V) of the power source voltage Vout_dig. A resistance value Rg in Expression (10) is the same as the resistance value Rg in Expression (7). A current value Ig in Expression (10) is calculated by adding the current value Idig and the current value Iana. The power source control unit 65 adjusts the value Vout_digc of the power source voltage Vout_dig such that the value of the distal end voltage Vcis_dig matches the target value Vtar_dig. The adjustment of the value Vout_digc is repeated, and the value of the distal end voltage Vcis_dig nears the target value Vtar_dig.

The following Expression (11) indicates a value Vout_anac of the power source voltage Vout_ana. The power source control unit 65 adjusts the value Vout_anac of the power source voltage Vout_ana in accordance with Expression (11) in Step S160.

$$V_{out\_anac}=R_{ana}I_{ana}+V_{tar\_ana}+R_{g}I_{g} \quad (11)$$

A resistance value Rana in Expression (11) is the same as the resistance value Rana in Expression (9). The current value Iana measured by the current measurement unit 63 is used in Expression (11). A value Vtar_ana in Expression (11) indicates a target value (for example, 2.7 V) of the power source voltage Vout_ana. The value Vtar_ana in Expression (11) is different from the value Vtar_dig in Expression (10). A resistance value Rg in Expression (11) is the same as the resistance value Rg in Expression (7). A current value Ig in Expression (11) is calculated by adding the current value Idig and the current value Iana. The power source control unit 65 adjusts the value Vout_anac of the power source voltage Vout_ana such that the value of the distal end voltage Vcis_ana matches the target value Vtar_ana. The target value Vtar_ana is different from the target value Vtar_dig. The adjustment of the value Vout_anac is repeated, and the value of the distal end voltage Vcis_ana nears the target value Vtar_ana.

The order in which Step S105 and Step S110 are executed may be different from that shown in FIG. 3. For example, after Step S110 is executed, Step S105 may be executed. After Step S115 is executed, at least one of Steps S105 and S110 may be executed.

Step S120 may be executed at any timing after Step S110 is executed and before Step S125 is executed.

The order in which Step S130 and Step S135 are executed may be different from that shown in FIG. 3. For example, after Step S135 is executed, Step S130 may be executed. After Step S140 is executed, at least one of Steps S130 and S135 may be executed.

Step S145 may be executed at any timing after Step S135 is executed and before Step S150 is executed.

Figure 5:
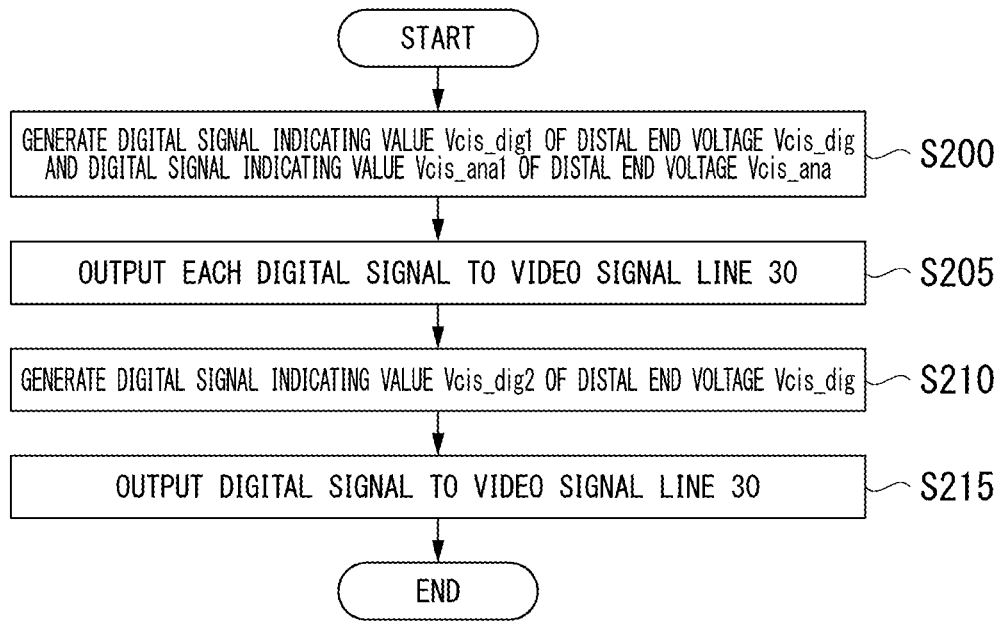
FIG. 5 is a flow chart showing a procedure of an operation of a camera device included in the endoscope system according to the first embodiment of the present invention.

FIG. 5 shows a procedure of an operation of the camera device 9 related to adjustment of the power source voltage Vout_dig and the power source voltage Vout_ana. The operation of the camera device 9 will be described by using FIG. 5.

The AD conversion unit 92 performs AD conversion on the distal end voltage Vcis_dig in the first period and generates a digital signal indicating a value Vcis_dig1 of the distal end voltage Vcis_dig. The AD conversion unit 92 performs AD conversion on the distal end voltage Vcis_ana in the first period and generates a digital signal indicating a value Vcis_ana1 of the distal end voltage Vcis_ana (Step S200).

After Step S200, the signal-processing unit 93 outputs each digital signal to the video signal line 30 (Step S205).

After Step S205, the AD conversion unit 92 performs AD conversion on the distal end voltage Vcis_dig in the second period and generates a digital signal indicating a value Vcis_dig2 of the distal end voltage Vcis_dig (Step S210).

After Step S210, the signal-processing unit 93 outputs the digital signal to the video signal line 30 (Step S215).

Each aspect of the present invention may include the following modified example. The image sensor 90 receives, as a distal end voltage Vcis_dig (first distal end voltage), a power source voltage Vout_dig (first power source voltage) output from the control unit 6 to the power source line 31 (first power source line). The image sensor 90 receives, as a distal end voltage Vcis_ana (second distal end voltage), a power source voltage Vout_ana (second power source voltage) output from the control unit 6 to the power source line 32 (second power source line). The value of the power source voltage Vout_ana is different from that of the power source voltage Vout_dig. The AD conversion unit 92 measures a value of the distal end voltage Vcis_dig and a value of the distal end voltage Vcis_ana. The signal-processing unit 93 outputs a first digital signal indicating the value of the distal end voltage Vcis_dig and a second digital signal indicating the value of the distal end voltage Vcis_ana to the video signal line 30. The power source unit 60 generates the power source voltage Vout_dig and the power source voltage Vout_ana. The power source unit 60 outputs the generated power source voltage Vout_dig to the power source line 31 and outputs the generated power source voltage Vout_ana to the power source line 32. The current measurement unit 63 measures a current value of the power source line 31 and a current value of the power source line 32. The AFE unit 50 receives the first digital signal and the second digital signal. The resistance calculation unit 64 calculates a resistance value of the power source line 31 based on the value of the power source voltage Vout_dig, the value of the distal end voltage Vcis_dig indicated by the first digital signal, the current value of the power source line 31, the resistance value of the ground line 33, and the current value of the ground line 33 (Expression (8)). The resistance calculation unit 64 calculates a resistance value of the power source line 32 based on the value of the power source voltage Vout_ana, the value of the distal end voltage Vcis_ana indicated by the second digital signal, the current value of the power source line 32, the resistance value of the ground line 33, and the current value of the ground line 33 (Expression (9)). The power source control unit 65 adjusts the value of the power source voltage Vout_dig based on the resistance value of the power source line 31, the current value of the power source line 31, the resistance value of the ground line 33, and the current value of the ground line 33 such that the value of the distal end voltage Vcis_dig nears a first target value (Expression (10)). The power source control unit 65 adjusts the value of the power source voltage Vout_ana based on the resistance value of the power source line 32, the current value of the power source line 32, the resistance value of the ground line 33, and the current value of the ground line 33 such that the value of the distal end voltage Vcis_ana nears a second target value (Expression (11)).

Each aspect of the present invention may include the following modified example. The resistance calculation unit 64 calculates the resistance value of the ground line 33 based on the value of the power source voltage Vout_dig (first power source voltage), the value of the distal end voltage Vcis_dig (first distal end voltage) indicated by the first digital signal, and the current value of the ground line 33 (Expression (7)).

Each aspect of the present invention may include the following modified example. The power source unit 60 outputs the power source voltage Vout_dig (first power source voltage) to the power source line 31 (first power source line) in a first period and a second period and outputs the power source voltage Vout_ana (second power source voltage) to the power source line 32 (second power source line) in the first period and the second period. A current value of the power source line 31 in the second period is the same as that of the power source line 31 in the first period. A current value of the power source line 32 in the second period is different from that of the power source line 32 in the first period. The resistance calculation unit 64 calculates the resistance value of the ground line 33 based on the value of the power source voltage Vout_dig in each of the first period and the second period, the value of the distal end voltage Vcis_dig (first distal end voltage) indicated by the first digital signal in each of the first period and the second period, and the current value of the ground line 33 in each of the first period and the second period (Expression (7)).

Each aspect of the present invention may include the following modified example. The first period and the second period are included in a blanking period of the image sensor 90.

Each aspect of the present invention may include the following modified example. The resistance calculation unit 64 calculates the current value of the ground line 33 based on the current value of the power source line 31 (first power source line) and the current value of the power source line 32 (second power source line).

Each aspect of the present invention may include the following modified example. One of the distal end voltage Vcis_dig (first distal end voltage) and the distal end voltage Vcis_ana (second distal end voltage) is provided to a digital circuit included in the image sensor 90. The other of the distal end voltage Vcis_dig and the distal end voltage Vcis_ana is provided to an analog circuit included in the image sensor 90.

In the first embodiment, the endoscope system 1 calculates the resistance value of the power source line 31 based on the value of the power source voltage Vout_dig, the value of the distal end voltage Vcis_dig, the current value of the power source line 31, the resistance value of the ground line 33, and the current value of the ground line 33. In addition, the endoscope system 1 calculates the resistance value of the power source line 32 based on the value of the power source voltage Vout_ana, the value of the distal end voltage Vcis_ana, the current value of the power source line 32, the resistance value of the ground line 33, and the current value of the ground line 33. Since the resistance value and the current value of the ground line 33 are considered, the endoscope system 1 can accurately calculate the resistance value of the power source line 31 and the resistance value of the power source line 32.

The endoscope system 1 adjusts the value of the power source voltage Vout_dig based on the resistance value of the power source line 31, the current value of the power source line 31, the resistance value of the ground line 33, and the current value of the ground line 33. In addition, the endoscope system 1 adjusts the value of the power source voltage Vout_ana based on the resistance value of the power source line 32, the current value of the power source line 32, the resistance value of the ground line 33, and the current value of the ground line 33. Since the resistance value and the current value of the ground line 33 are considered, the endoscope system 1 can accurately adjust the value of the power source voltage Vout_dig and the value of the power source voltage Vout_ana.

Modified Example of First Embodiment

A modified example of the first embodiment of the present invention will be described. In the modified example of the first embodiment, a method of calculating a resistance value of the ground line 33 is different from that in the first embodiment.

Figure 6:
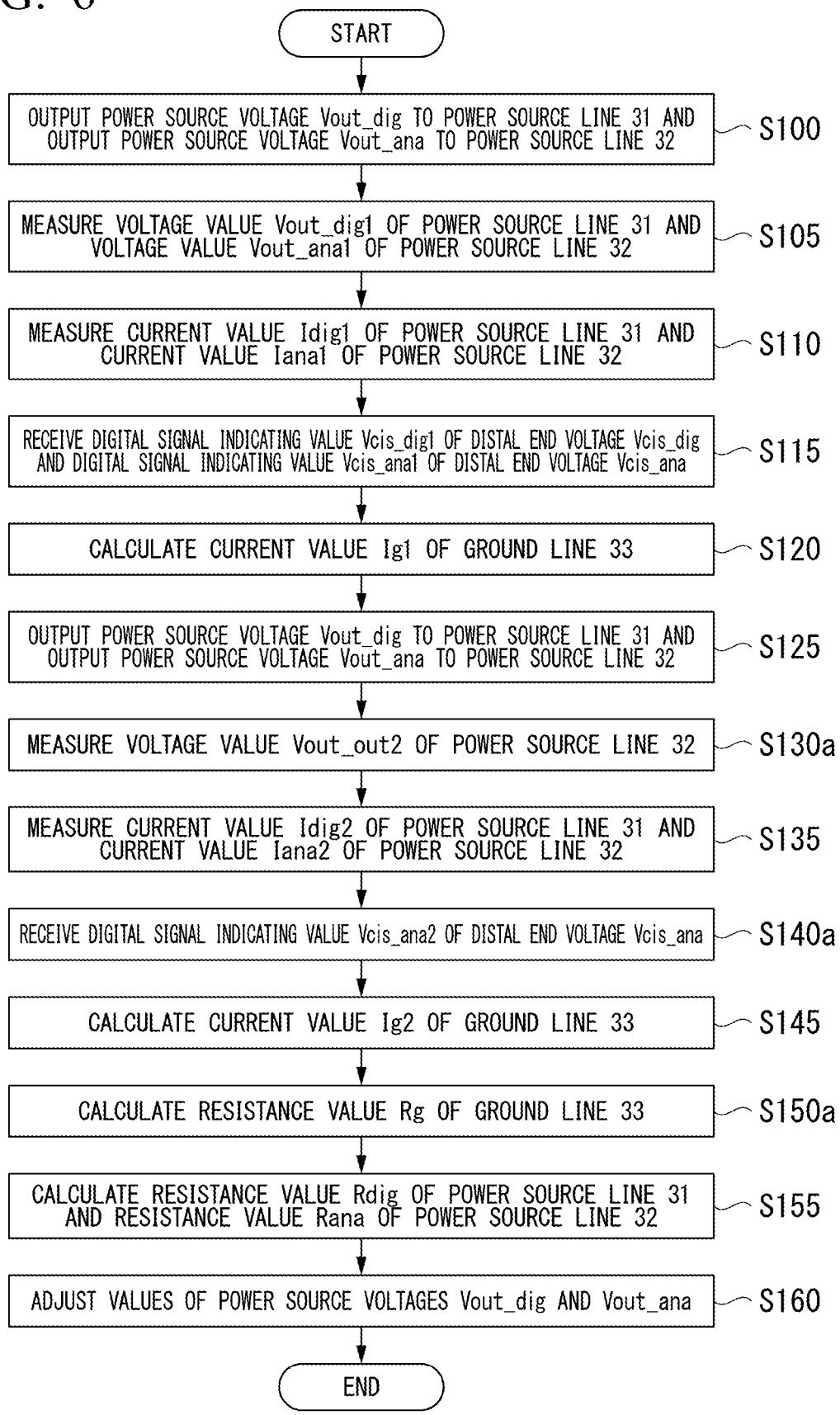
FIG. 6 is a flow chart showing a procedure of an operation of a control unit included in an endoscope system according to a modified example of the first embodiment of the present invention.

FIG. 6 shows a procedure of an operation of the control unit 6 related to adjustment of the power source voltage Vout_dig and the power source voltage Vout_ana. The operation of the control unit 6 will be described by using FIG. 6. Descriptions of the same processing as that shown in FIG. 3 will be omitted.

After Step S125, the voltage measurement unit 62 measures a value Vout_ana2 of the power source voltage Vout_ana in the power source line 32 and outputs the value Vout_ana2 to the resistance calculation unit 64 (Step S130a). After Step S130a, Step S135 is executed.

After Step S135, the AFE unit 50 receives a digital signal transferred by the video signal line 30 and processes the digital signal. The digital signal indicates a value Vcis_ana2 of the distal end voltage Vcis_ana in the second period. The digital signal is output to the signal-processing unit 51. The signal-processing unit 51 processes the digital signal and outputs the digital signal to the resistance calculation unit 64 (Step S140a). After Step S140a, Step S145 is executed.

Figure 7:
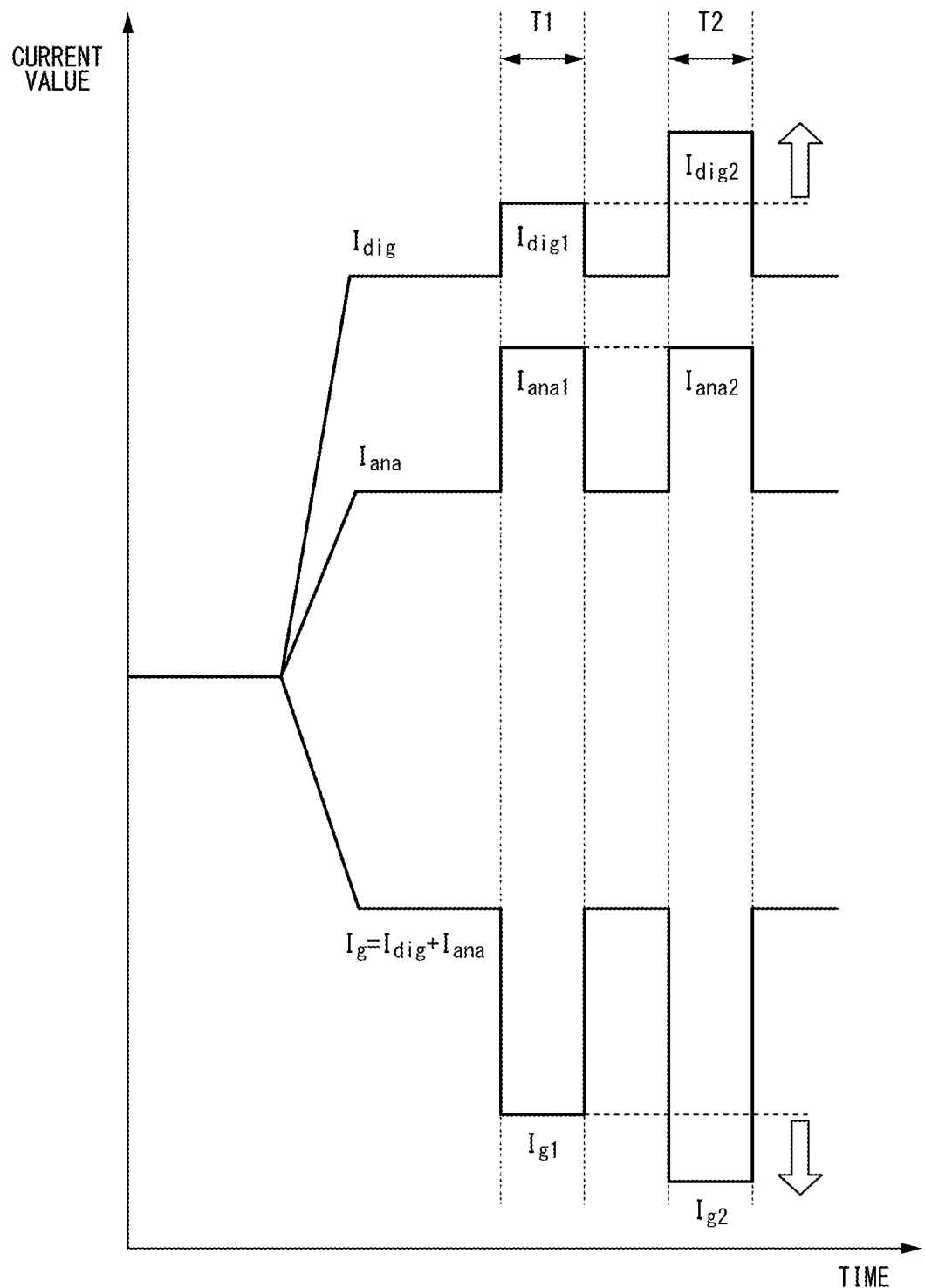
FIG. 7 is a timing chart showing waveforms of currents flowing through a transmission cable included in the endoscope system according to the modified example of the first embodiment of the present invention.

FIG. 7 shows waveforms of the current Idig, the current Iana, and the current Ig. The horizontal axis in FIG. 7 indicates time, and the vertical axis in FIG. 7 indicates a current value.

The power source unit 60 outputs the power source voltage Vout_ana to the power source line 32 such that a value Iana1 of the current Iana in a first period T1 and a value Iana2 of the current Iana in a second period T2 are the same. For example, a value Vout_ana2 of the power source voltage Vout_ana in the second period T2 is the same as a value Vout_ana1 of the power source voltage Vout_ana in the first period T1.

The power source unit 60 outputs the power source voltage Vout_dig to the power source line 31 such that a value Idig1 of the current Idig in the first period T1 and a value Idig2 of the current Idig in the second period T2 are different. For example, a value Vout_dig2 of the power source voltage Vout_dig in the second period T2 is different from a value Vout_dig1 of the power source voltage Vout_dig in the first period T1.

In the example shown in FIG. 7, the value Idig2 of the current Idig in the second period T2 is greater than the value Idig1 of the current Idig in the first period T1. The value Idig2 of the current Idig in the second period T2 may be less than the value Idig1 of the current Idig in the first period T1.

The current Ig is the sum of the current Idig and the current Iana. The value of the current Ig in the first period T1 is Ig1, and the value of the current Ig in the second period T2 is Ig2.

After Step S145, the resistance calculation unit 64 calculates a resistance value Rg of the ground line 33 based on the values Vout_ana1 and Vout_ana2 of the power source voltage Vout_ana, the values Vcis_ana1 and Vcis_ana2 of the distal end voltage Vcis_ana, and the current values Ig1 and Ig2 of the ground line 33 (Step S150a). After Step S150a, Step S155 is executed.

The following Expression (12) is obtained by using a similar method to that by which Expression (6) is obtained from Expression (4) and Expression (5).

$$V_{out\_ana1} - V_{out\_ana2} = (V_{cis\_ana1} - V_{cis\_ana2}) + R_g(I_{g1} - I_{g2}) \quad (12)$$

By modifying Expression (12), the following Expression (13) is obtained. The resistance calculation unit 64 calculates the resistance value Rg of the ground line 33 in accordance with Expression (13) in Step S150a.

$$R_g = \frac{(V_{out\_ana1} - V_{out\_ana2}) - (V_{cis\_ana1} - V_{cis\_ana2})}{I_{g1} - I_{g2}} \quad (13)$$

Figure 8:
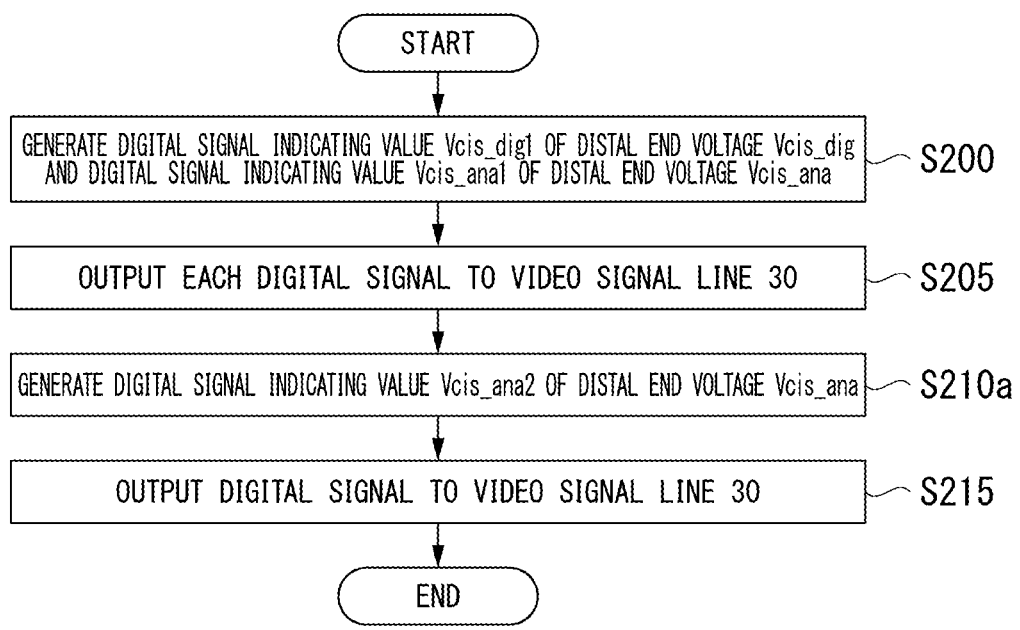
FIG. 8 is a flow chart showing a procedure of an operation of a camera device included in the endoscope system according to the modified example of the first embodiment of the present invention.

FIG. 8 shows a procedure of an operation of the camera device 9 related to adjustment of the power source voltage Vout_dig and the power source voltage Vout_ana. The operation of the camera device 9 will be described by using FIG. 8. The same processing as that shown in FIG. 5 will be omitted.

After Step S205, the AD conversion unit 92 performs AD conversion on the distal end voltage Vcis_ana in the second period and generates a digital signal indicating a value Vcis_ana2 of the distal end voltage Vcis_ana (Step S210a). After Step S210a, Step S215 is executed.

Each aspect of the present invention may include the following modified example. The image sensor 90 receives, as a distal end voltage Vcis_ana (first distal end voltage), a power source voltage Vout_ana (first power source voltage) output from the control unit 6 to the power source line 32 (first power source line). The image sensor 90 receives, as a distal end voltage Vcis_dig (second distal end voltage), a power source voltage Vout_dig (second power source voltage) output from the control unit 6 to the power source line 31 (second power source line). The value of the power source voltage Vout_dig is different from that of the power source voltage Vout_ana. The AD conversion unit 92 measures a value of the distal end voltage Vcis_ana and a value of the distal end voltage Vcis_dig. The signal-processing unit 93 outputs a first digital signal indicating the value of the distal end voltage Vcis_ana and a second digital signal indicating the value of the distal end voltage Vcis_dig to the video signal line 30. The power source unit 60 generates the power source voltage Vout_ana and the power source voltage Vout_dig. The power source unit 60 outputs the generated power source voltage Vout_ana to the power source line 32 and outputs the generated power source voltage Vout_dig to the power source line 31. The current measurement unit 63 measures a current value of the power source line 32 and a current value of the power source line 31. The AFE unit 50 receives the first digital signal and the second digital signal. The resistance calculation unit 64 calculates a resistance value of the power source line 32 based on the value of the power source voltage Vout_ana, the value of the distal end voltage Vcis_ana indicated by the first digital signal, the current value of the power source line 32, the resistance value of the ground line 33, and the current value of the ground line 33 (Expression (9)). The resistance calculation unit 64 calculates a resistance value of the power source line 31 based on the value of the power source voltage Vout_dig, the value of the distal end voltage Vcis_dig indicated by the second digital signal, the current value of the power source line 31, the resistance value of the ground line 33, and the current value of the ground line 33 (Expression (8)). The power source control unit 65 adjusts the value of the power source voltage Vout_ana based on the resistance value of the power source line 32, the current value of the power source line 32, the resistance value of the ground line 33, and the current value of the ground line 33 such that the value of the distal end voltage Vcis_ana nears a first target value (Expression (11)). The power source control unit 65 adjusts the value of the power source voltage Vout_dig based on the resistance value of the power source line 31, the current value of the power source line 31, the resistance value of the ground line 33, and the current value of the ground line 33 such that the value of the distal end voltage Vcis_dig nears a second target value (Expression (10)).

Each aspect of the present invention may include the following modified example. The resistance calculation unit 64 calculates a resistance value of the ground line 33 based on the value of the power source voltage Vout_ana (first power source voltage), the value of the distal end voltage Vcis_ana (first distal end voltage) indicated by the first digital signal, and the current value of the ground line 33 (Expression (13)).

Each aspect of the present invention may include the following modified example. The power source unit 60 outputs the power source voltage Vout_ana (first power source voltage) to the power source line 32 (first power source line) in a first period and a second period and outputs the power source voltage Vout_dig (second power source voltage) to the power source line 31 (second power source line) in the first period and the second period. A current value of the power source line 32 in the second period is the same as that of the power source line 32 in the first period. A current value of the power source line 31 in the second period is different from that of the power source line 31 in the first period. The resistance calculation unit 64 calculates the resistance value of the ground line 33 based on the value of the power source voltage Vout_ana in each of the first period and the second period, the value of the distal end voltage Vcis_ana (first distal end voltage) indicated by the first digital signal in each of the first period and the second period, and the current value of the ground line 33 in each of the first period and the second period (Expression (13)).

Each aspect of the present invention may include the following modified example. The first period and the second period are included in a blanking period of the image sensor 90.

Each aspect of the present invention may include the following modified example. The resistance calculation unit 64 calculates the current value of the ground line 33 based on the current value of the power source line 32 (first power source line) and the current value of the power source line 31 (second power source line).

In the modified example of the first embodiment, the endoscope system 1 can accurately calculate the resistance value of the power source line 31 and the resistance value of the power source line 32 as in the first embodiment. In addition, the endoscope system 1 can accurately adjust the value of the power source voltage Vout_dig and the value of the power source voltage Vout_ana as in the first embodiment.

Second Embodiment

A second embodiment of the present invention will be described. In the second embodiment, the endoscope system 1 shown in FIG. 1 and FIG. 2 is used.

The conductivity of the ground line 33 is the same as that of the power source line 31. The diameter of the ground line 33 is the same as that of the power source line 31. The length of the ground line 33 is the same as that of the power source line 31. If these conditions are met, the resistance value of the ground line 33 may be regarded as being the same as that of the power source line 31.

Figure 9:
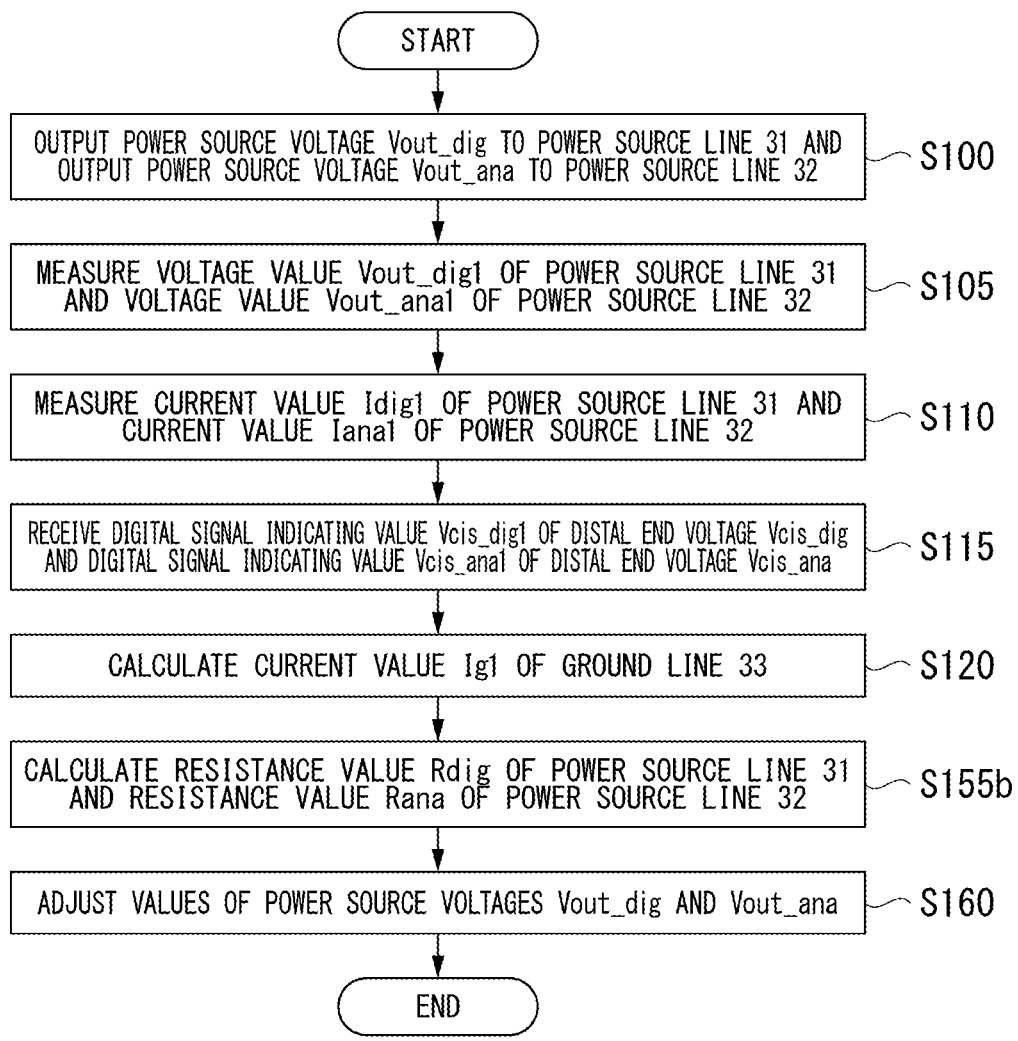
FIG. 9 is a flow chart showing a procedure of an operation of a control unit included in an endoscope system according to a second embodiment of the present invention.

FIG. 9 shows a procedure of an operation of the control unit 6 related to adjustment of the power source voltage Vout_dig and the power source voltage Vout_ana. The operation of the control unit 6 under the condition that the resistance value of the ground line 33 is the same as that of the power source line 31 will be described by using FIG. 9. Descriptions of the same processing as that shown in FIG. 3 will be omitted.

After Step S120, the resistance calculation unit 64 calculates the resistance value Rdig of the power source line 31 based on the value of the power source voltage Vout_dig, the value of the distal end voltage Vcis_dig, the current value of the power source line 31, and the current value Ig of the ground line 33. In addition, the resistance calculation unit 64 calculates the resistance value Rana of the power source line 32 based on the value of the power source voltage Vout_ana, the value of the distal end voltage Vcis_ana, the current value of the power source line 32, and the current value Ig of the ground line 33. The resistance calculation unit 64 outputs the resistance value Rdig of the power source line 31 and the resistance value Rana of the power source line 32 to the power source control unit 65 (Step S155b). After Step S155b, Step S160 is executed.

When the resistance value of the ground line 33 is the same as that of the power source line 31, Expression (8) described above is changed to the following Expression (14). The resistance calculation unit 64 calculates the resistance value Rdig of the power source line 31 in accordance with Expression (14) in Step S155b.

$$R_{dig} = \frac{V_{out\_dig1} - V_{cis\_dig1}}{I_{dig1} + I_{g1}} \quad (14)$$

The resistance calculation unit 64 calculates the resistance value Rana of the power source line 32 in accordance with Expression (9) described above in Step S155b. The resistance value Rg in Expression (9) is the same as the resistance value Rdig of the power source line 31.

The camera device 9 executes Step S200 and Step S205 shown in FIG. 5, but does not need to execute Step S210 and Step S215 shown in FIG. 5.

The resistance calculation unit 64 may calculate a ratio Kdig (=Rg/Rdig) between the resistance value Rg of the ground line 33 and the resistance value Rdig of the power source line 31 based on the conductivity of the ground line 33, the conductivity of the power source line 31, the diameter of the ground line 33, the diameter of the power source line 31, the length of the ground line 33, and the length of the power source line 31. The resistance calculation unit 64 may calculate the resistance value Rdig of the power source line 31 in accordance with the following Expression (15) in Step S155b.

$$R_{dig} = \frac{V_{out\_dig1} - V_{cis\_dig1}}{I_{dig1} + K_{dig}I_{g1}} \quad (15)$$

In the second embodiment, the endoscope system 1 does not need to execute the processing in the second period described above. Therefore, the endoscope system 1 can shorten the processing time required for adjusting the power source voltage Vout_dig and the power source voltage Vout_ana.

Modified Example of Second Embodiment

A modified example of the second embodiment of the present invention will be described. The conductivity of the ground line 33 is the same as that of the power source line 32. The diameter of the ground line 33 is the same as that of the power source line 32. The length of the ground line 33 is the same as that of the power source line 32. If these conditions are met, the resistance value of the ground line 33 may be regarded as being the same as that of the power source line 32.

When the resistance value of the ground line 33 is the same as that of the power source line 32, Expression (9) described above is changed to the following Expression (16). The resistance calculation unit 64 calculates the resistance value Rana of the power source line 32 in accordance with Expression (16) in Step S155b.

$$R_{ana} = \frac{V_{out\_ana1} - V_{cis\_ana1}}{I_{ana1} + I_{g1}} \quad (16)$$

The resistance calculation unit 64 calculates the resistance value Rdig of the power source line 31 in accordance with Expression (8) described above in Step S155b. The resistance value Rg in Expression (8) is the same as the resistance value Rana of the power source line 32.

The resistance calculation unit 64 may calculate a ratio Kana (=Rg/Rana) between the resistance value Rg of the ground line 33 and the resistance value Rana of the power source line 32 based on the conductivity of the ground line 33, the conductivity of the power source line 32, the diameter of the ground line 33, the diameter of the power source line 32, the length of the ground line 33, and the length of the power source line 32. The resistance calculation unit 64 may calculate the resistance value Rana of the power source line 32 in accordance with the following Expression (17) in Step S155b.

$$R_{ana} = \frac{V_{out\_ana1} - V_{cis\_ana1}}{I_{ana1} + K_{ana}I_{g1}} \quad (17)$$

In the modified example of the second embodiment, the endoscope system 1 can shorten the processing time required for adjusting the power source voltage Vout_dig and the power source voltage Vout_ana as in the second embodiment described above.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging system, comprising a camera device and a control device connected to each other by a power source line, a video signal line, and a ground line,
the camera device including:
an image sensor that receives, as a distal end voltage, a power source voltage output from the control device to the power source line and generates a video signal by using the distal end voltage;
a voltage measurement circuit that measures a value of the distal end voltage; and
an output circuit that outputs the video signal to the video signal line and outputs a digital signal indicating the value of the distal end voltage to the video signal line, and
the control device including:
a voltage generation circuit that generates the power source voltage and outputs the generated power source voltage to the power source line;
a current measurement circuit that measures a current value of the power source line;
a reception circuit that receives the video signal and the digital signal output from the camera device to the video signal line;
a calculation circuit that calculates a resistance value of the power source line based on a value of the power source voltage, the value of the distal end voltage indicated by the digital signal, the current value of the power source line, a resistance value of the ground line, and a current value of the ground line; and
a voltage adjustment circuit that adjusts a value of the power source voltage based on the resistance value of the power source line, the current value of the power source line, the resistance value of the ground line, and the current value of the ground line such that the value of the distal end voltage nears a target value.

2. The imaging system according to claim 1,
wherein the power source line includes a first power source line and a second power source line,
wherein the image sensor receives, as a first distal end voltage, a first power source voltage output from the control device to the first power source line and receives, as a second distal end voltage, a second power source voltage output from the control device to the second power source line,
wherein a value of the second power source voltage is different from a value of the first power source voltage,
wherein the voltage measurement circuit measures a value of the first distal end voltage and a value of the second distal end voltage,
wherein the output circuit outputs a first digital signal indicating the value of the first distal end voltage and a second digital signal indicating the value of the second distal end voltage to the video signal line,
wherein the voltage generation circuit generates the first power source voltage and the second power source voltage, outputs the generated first power source voltage to the first power source line, and outputs the generated second power source voltage to the second power source line,
wherein the current measurement circuit measures a current value of the first power source line and a current value of the second power source line,
wherein the reception circuit receives the first digital signal and the second digital signal,
wherein the calculation circuit calculates a resistance value of the first power source line based on the value of the first power source voltage, the value of the first distal end voltage indicated by the first digital signal, the current value of the first power source line, the resistance value of the ground line, and the current value of the ground line,
wherein the calculation circuit calculates a resistance value of the second power source line based on the value of the second power source voltage, the value of the second distal end voltage indicated by the second digital signal, the current value of the second power source line, the resistance value of the ground line, and the current value of the ground line,
wherein the voltage adjustment circuit adjusts the value of the first power source voltage based on the resistance value of the first power source line, the current value of the first power source line, the resistance value of the ground line, and the current value of the ground line such that the value of the first distal end voltage nears a first target value, and
wherein the voltage adjustment circuit adjusts the value of the second power source voltage based on the resistance value of the second power source line, the current value of the second power source line, the resistance value of the ground line, and the current value of the ground line such that the value of the second distal end voltage nears a second target value.

3. The imaging system according to claim 2,
wherein the calculation circuit calculates the resistance value of the ground line based on the value of the first power source voltage, the value of the first distal end voltage indicated by the first digital signal, and the current value of the ground line.

4. The imaging system according to claim 2,
wherein the voltage generation circuit outputs the first power source voltage to the first power source line in a first period and a second period and outputs the second power source voltage to the second power source line in the first period and the second period, wherein a current value of the first power source line in the second period is the same as a current value of the first power source line in the first period, wherein a current value of the second power source line in the second period is different from a current value of the second power source line in the first period, and wherein the calculation circuit calculates the resistance value of the ground line based on the value of the first power source voltage in each of the first period and the second period, the value of the first distal end voltage indicated by the first digital signal in each of the first period and the second period, and the current value of the ground line in each of the first period and the second period.

5. The imaging system according to claim 4,
wherein the first period and the second are included in a blanking period of the image sensor.

6. The imaging system according to claim 2,
wherein the calculation circuit calculates the current value of the ground line based on the current value of the first power source line and the current value of the second power source line.

7. The imaging system according to claim 2,
wherein one of the first distal end voltage and the second distal end voltage is provided to a digital circuit included in the image sensor, and
wherein the other of the first distal end voltage and the second distal end voltage is provided to an analog circuit included in the image sensor.

8. The imaging system according to claim 1,
wherein the resistance value of the ground line is the same as the resistance value of the power source line.

9. An endoscope system, comprising
a scope to be inserted into a living body; and
the imaging system according to claim 1,
wherein the camera device is disposed in a distal end of the scope.

10. A control device in an imaging system including a camera device and the control device connected to each other by a power source line, a video signal line, and a ground line, the control device comprising:
 a voltage generation circuit that generates a power source voltage and outputs the generated power source voltage to the power source line;
 a current measurement circuit that measures a current value of the power source line;
 a reception circuit that receives a video signal and a digital signal output from the camera device to the video signal line,
  wherein the video signal is generated by an image sensor of the camera device,
  wherein the image sensor receives, as a distal end voltage, the power source voltage output from the control device to the power source line and generates the video signal by using the distal end voltage, and
  wherein the digital signal indicates a value of the distal end voltage;
 a calculation circuit that calculates a resistance value of the power source line based on a value of the power source voltage, the value of the distal end voltage indicated by the digital signal, the current value of the power source line, a resistance value of the ground line, and a current value of the ground line; and
 a voltage adjustment circuit that adjusts a value of the power source voltage based on the resistance value of the power source line, the current value of the power source line, the resistance value of the ground line, and the current value of the ground line such that the value of the distal end voltage nears a target value.

* * * * *